(12) United States Patent
Maranhao (10) Patent No.: US 8,852,924 B2
(45) Date of Patent: Oct. 7, 2014

(54) ALGAE PHOTOBIOREACTOR

(75) Inventor: Andre Camarate de Albuquerque Maranhao, Irvine, CA (US)

(73) Assignee: Chingoo Research Partnership, Irvine, CA (US)

( * ) Notice: Subject to any disclaimer, the term of this patent is extended or adjusted under 35 U.S.C. 154(b) by 718 days.

(21) Appl. No.: 12/750,170

(22) Filed: Mar. 30, 2010

(65) Prior Publication Data

US 2010/0255569 A1 Oct. 7, 2010

Related U.S. Application Data

(60) Provisional application No. 61/166,111, filed on Apr. 2, 2009.

(51) Int. Cl.
*C12M 3/02* (2006.01)
*C12M 1/00* (2006.01)

(52) U.S. Cl.
CPC .............. *C12M 21/02* (2013.01); *C12M 23/22* (2013.01); *C12M 29/00* (2013.01); *C12M 23/38* (2013.01); *C12M 27/22* (2013.01); *C12M 29/18* (2013.01)
USPC .................. 435/292.1; 435/295.2; 435/294.1; 435/291.4

(58) Field of Classification Search
USPC ...................... 435/292.1, 295.2, 294.1, 291.4
See application file for complete search history.

(56) References Cited

U.S. PATENT DOCUMENTS

| | | | |
|---|---|---|---|
| 2,732,663 A | 1/1956 | Dewey, II | |
| 2,866,297 A | 12/1958 | Marissal | |
| 3,362,104 A | 1/1968 | Oswald et al. | |
| 3,520,081 A | 7/1970 | Oswald et al. | |
| 3,959,923 A | 6/1976 | Selke | |
| 4,003,160 A | 1/1977 | Müller | |
| 4,233,958 A | 11/1980 | Heden | |
| 4,555,864 A | 12/1985 | Mori | |
| 4,690,697 A | 9/1987 | Schwartz et al. | |
| 4,868,123 A | 9/1989 | Berson et al. | |
| 4,869,824 A * | 9/1989 | Melin et al. .................... 210/615 |
| 6,346,412 B1 * | 2/2002 | Stormo ........................ 435/262 |
| 6,348,347 B1 | 2/2002 | Hirabayashi et al. | |
| 6,509,188 B1 * | 1/2003 | Trosch et al. .............. 435/292.1 |
| 6,579,714 B1 | 6/2003 | Hirabayashi et al. | |

(Continued)

OTHER PUBLICATIONS

International Search Report and Written Opinion for International Application No. PCT/US10/29695, mailed Jun. 9, 2010, 9 pages.

*Primary Examiner* — William H Beisner
*Assistant Examiner* — Danielle Henkel
(74) *Attorney, Agent, or Firm* — Christie, Parker & Hale, LLP (57) ABSTRACT

A closed transparent photobioreactor having a dome and a staged column wherein the dome is used as a growth chamber to provide a large culture volume to land area used and a flow pattern inside the dome allows for the uniform distribution of light energy, thereby negating growth rate inhibiting 'dark zones'. A pump delivers culture from the bottom of the column to a lower portion of the dome and drives circulation between the two components and an increase in mass in the dome results in a spillover from the top of the dome into the column. Once in the column, algaculture will be aerated at each stage before returning to the dome. The staged column also provides for semi-continuous harvest of algae through the application of froth flotation and various other separation processes.

12 Claims, 6 Drawing Sheets

(56) References Cited

U.S. PATENT DOCUMENTS

| | | | |
|---|---|---|---|
| 6,631,892 B1* | 10/2003 | Erickson | 261/114.1 |
| 2004/0029267 A1* | 2/2004 | Martin et al. | 435/299.1 |
| 2007/0155006 A1* | 7/2007 | Levin | 435/292.1 |
| 2007/0289206 A1 | 12/2007 | Kertz | |
| 2008/0009055 A1 | 1/2008 | Lewnard | |
| 2008/0153080 A1 | 6/2008 | Woods et al. | |
| 2008/0155890 A1 | 7/2008 | Oyler | |
| 2008/0160591 A1* | 7/2008 | Willson et al. | 435/132 |
| 2008/0178739 A1* | 7/2008 | Lewnard et al. | 95/186 |
| 2008/0274494 A1 | 11/2008 | Kertz | |
| 2008/0299643 A1 | 12/2008 | Howard et al. | |
| 2009/0081723 A1* | 3/2009 | Amano et al. | 435/41 |

\* cited by examiner

ALGAE PHOTOBIOREACTOR

CROSS-REFERENCE TO RELATED APPLICATION(S)

This Application claims priority to U.S. Provisional Application No. 61/166,111, filed Apr. 2, 2009, the contents of which are incorporated herein by reference.

FIELD OF THE INVENTION

The present invention relates to the field of photobioreactors. More specifically, the invention is a photobioreactor device, its unique multifaceted and adaptable design, and a process for the cultivation and harvest of photosynthetic microorganisms, such as microalgae.

BACKGROUND OF THE INVENTION

The growing demand for liquid fuels and increasingly difficult means of supplying petroleum have led to the interest in biofuels. This umbrella term is applied to any form of energy that is ultimately derived from solar energy via photosynthesis. Despite their many promises, concerns have been raised about biofuels' feasibility, scale, and overall energy balance, as well as many ethical issues surrounding those that are also farmed for food. Many believe that algae represent the best crop for the biofuels of the future.

The events leading from light to liquid fuel can be organized into a series of phases. These phases are growth, separation, extraction, and refinement. The growth of algae can be accomplished through the use of a photobioreactor, or PBR. Photobioreactor is the generic term for the device used to cultivate a photosynthetic organism, such as algae. Once an algaculture has been grown it must be separated from the growth media. There are many means of algae harvest available and with any option there will be a tradeoff between efficiency and energy input. The extraction of hydrocarbons from the harvested algae represents the final phase for the 'algal farm'. Extracted hydrocarbons can then be packaged and transported to refinement facilities for processing into biodiesel, pyrolytic hydrocracking or any other conversion.

Many different concerns must be addressed when designing a PBR; chief among them is the availability and intensity of light. Light will dictate the size and location of the PBR. The need to introduce adequate levels of CO2 and remove produced O2 presents another set of design restrictions. Beyond these, there are secondary concerns that must be addressed including media selection, materials used, agitation system, and sterility. Open-air PBRs suffer from increased susceptibility to contamination and water loss through evaporation. Closed PBRs not only circumvent these detrimental problems, they also afford the ability to better control the conditions of the algaculture. There are many different designs available for closed PBRs, but the most popular is the tubular PBR. This simple system involves pumping algaculture through a transparent tube that is exposed to sunlight. The tube can be arranged in many different ways to best utilize space, light availability and gas transfer. A common motif with tubular PBRs is to build a 'fence' of tubes. Other designs include a figure-eight arrangement and a right triangle where gas pumped at the lower end of the hypotenuse drives the flow of algaculture up the hypotenuse providing circulation. Though these designs have valid concepts, they are lacking in many respects, namely overall algaculture volume, ratio of algaculture volume to material used, ratio of algaculture volume to land area used, gas mass transfer capabilities, and ease of harvest.

In order to address all these issues while still preserving the positive qualities of the tubular PBR, a novel PBR is proposed that has design considerations for every concern addressed.

SUMMARY OF THE INVENTION

The present invention seeks to create a system capable of providing all the components necessary to maximize overall production while maintaining reduced overhead costs. As such, the invention is a novel amalgamation of PBR design elements and chemical engineering principles. In its most basic form, the design is a closed, hollow dome that is filled with algaculture. This dome has an internal agitation system that will circulate the algaculture so as to provide a uniform light distribution. A spillover tube attached to the top of the dome will allow for spillover of algaculture into a trayed column. The purpose of the column is to provide an excellent means of mass transfer between gas phase and algaculture. The column also provides a means of accomplishing low cost harvest of algae that can either be continuous or semi-continuous. After the algaculture has run its course through the column, the aerated algaculture will be pumped into the dome. As presented, the invention can be thought of as a two-component system; the dome and the column. However, there are many variables to be considered for each component.

DETAILED DESCRIPTION OF THE DRAWINGS

Shape, Sizing, and Course of the Algaculture

Figure 1:
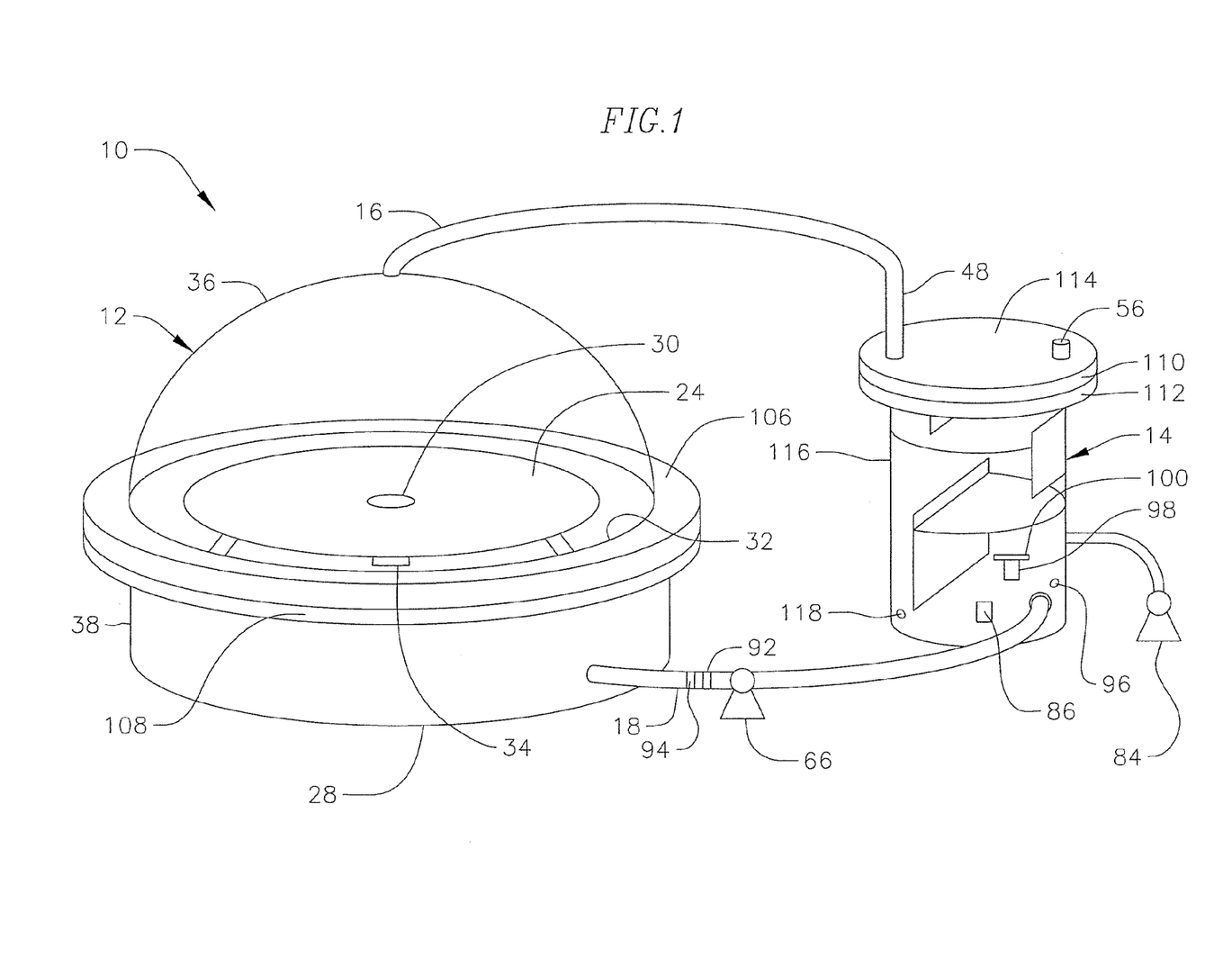
FIG. 1 is a perspective view of a photobioreactor of the present invention having a transparent ellipsoidal dome fixed to a rigid base with internal circular disk and submersible pump connected to a cylindrical trayed column by two tubes.
Figure 2:
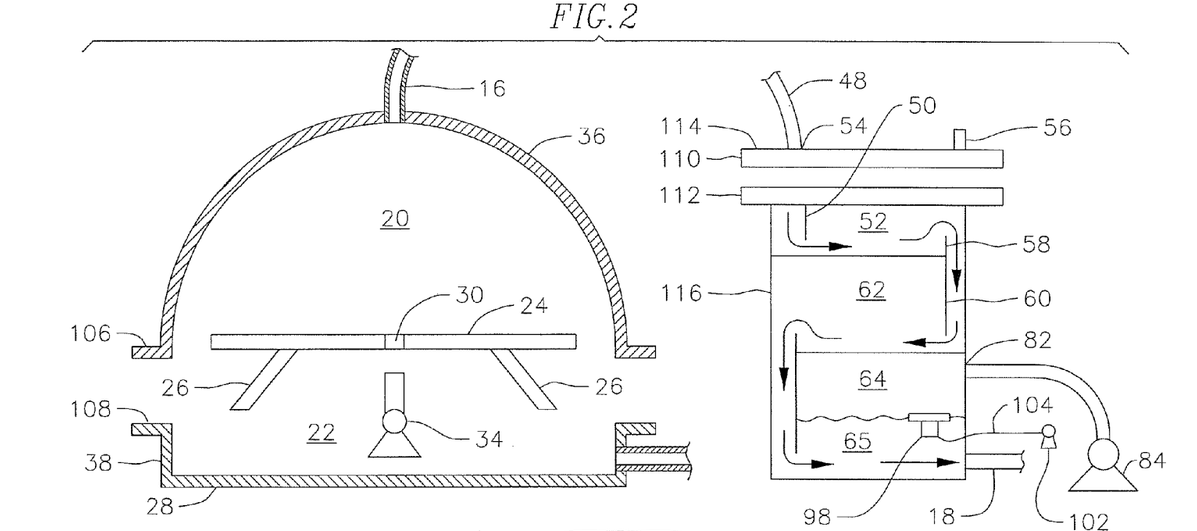
FIG. 2 is an exploded cross-sectional view the photobioreactor of FIG. 1.
Figure 3:
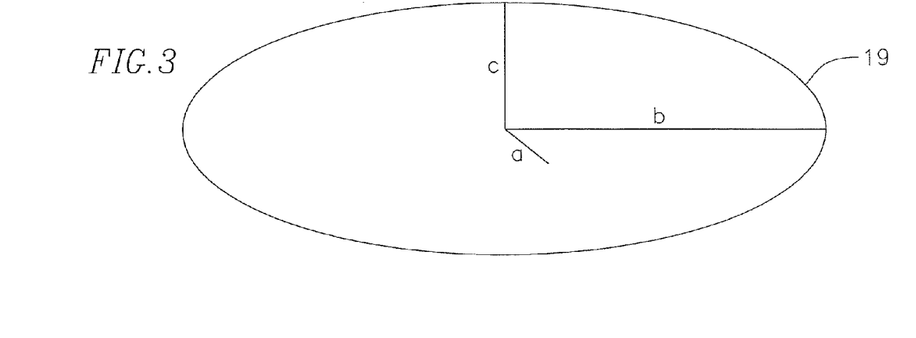
FIG. 3 is a schematic of an ellipsoid with three variable radii wherein the transparent dome of FIG. 1 can take on any shape from a hemi-ellipsoid.

Referring to FIGS. 1 and 2, an algae photobioreactor 10 of the present invention is illustrated. The photobioreactor or PBR 10 comprises a dome 12 and a column 14 connected by tubes 16 and 18. The dome 12 represents the growth chamber of the PBR. The shape and dimensions of the dome are both variable. The generic shape of the dome is the volume resulting from the equatorial truncation of an ellipsoid; one example being a hemi-ellipsoid. The relative proportions of equatorial and polar radii (a, b and c respectively) can also be varied in order to effect different results from the growth chamber. A sketch of an ellipsoid 19 can be seen in FIG. 3. Some of these effects include altering the flow pattern of the algaculture in the growth chamber as well as changing the light distribution in the chamber, as a result of changes to size and shape. In its most basic form, the dome is a hollow hemisphere; where a=b=c and the truncation is taken at the equatorial plane of symmetry. However, the dome can also take on the dimensions of a truncated spheroid, truncated oblate spheroid, truncated prolate spheroid or a truncated scalene ellipsoid. In the most basic forms of these possible dome shapes, the truncation is taken at the equatorial plane resulting in a hemisphere, hemi-oblate spheroid, hemi-prolate spheroid, and a hemi-scalene ellipsoid.

Once the optimal truncated ellipsoid dimensions have been obtained, the size of the dome can be varied in accordance with the optimal operational parameters. Light penetration represents the most important factor when sizing the dome. Light penetration and dome size will determine the illuminated fraction of the dome. Though most closed PBRs aim at illuminated fractions of one, PBR design restrictions of this sort lead to improper utilization of land and other problems previously discussed. Illuminated fractions lower than one can still prove productive if a novel circulation system is in place. This circulation system will be discussed shortly. In determining size, it becomes necessary to establish an operational ceiling for the concentration of algae grown before harvest; generally quantified by an optical density (OD) reading from a spectrophotometer. The cost effectiveness of harvest and the overall growth rate of culture at different OD readings determine the OD at which harvest should be carried out. Interestingly, the overall growth rate of a culture varies with respect to the illuminated fraction. This means that the sizing of any dome of hemi-ellipsoid shape can only be determined through experimentation. This sizing will also vary between algal species, so sizing experiments must be carried out on a case by case basis for any species prior to operational cultivation.

Figure 4:
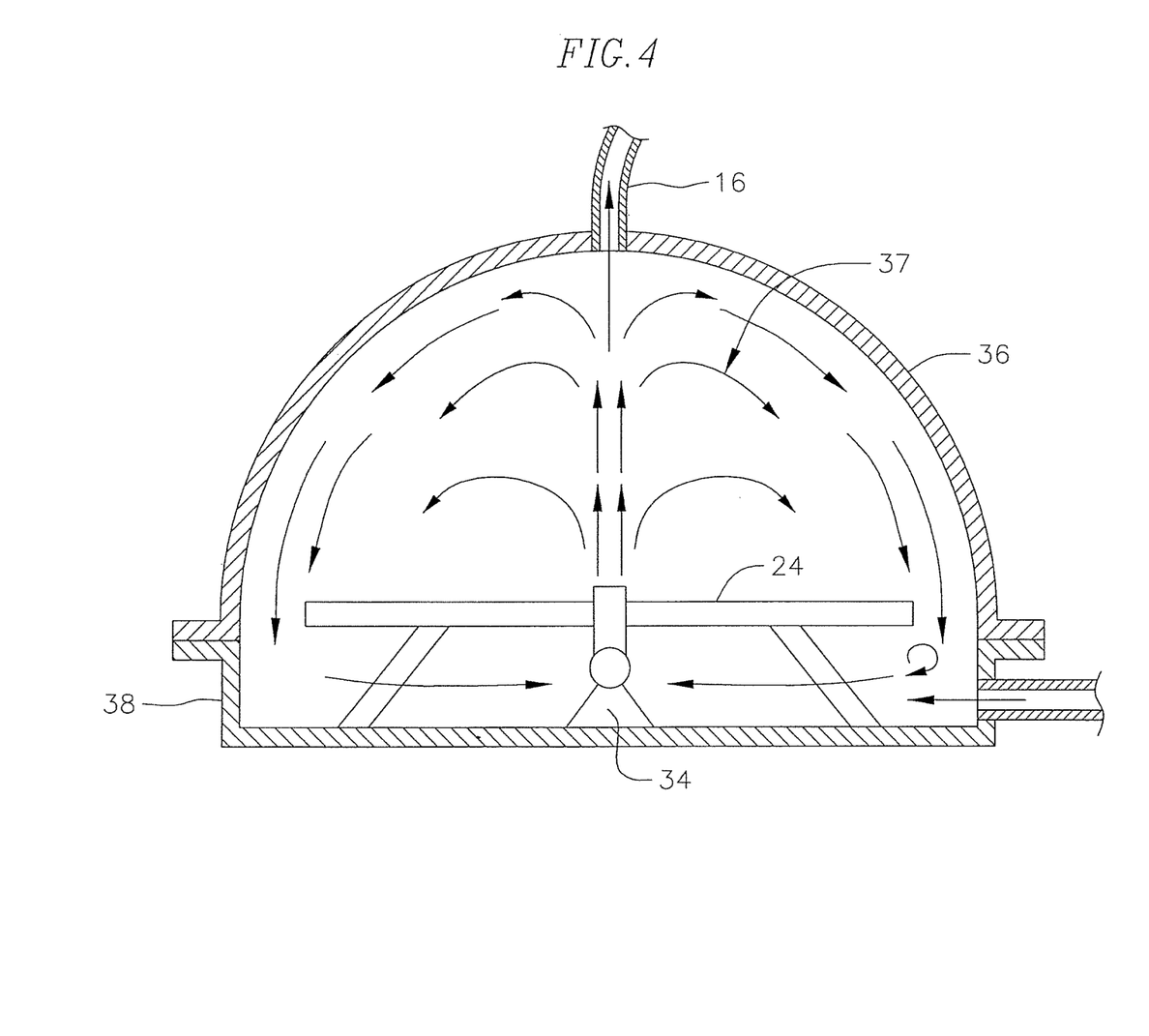
FIG. 4 is a cross-sectional view of the dome of FIG. 1 illustrating the novel flow pattern generated by the internal submersible pump.
Figure 5:
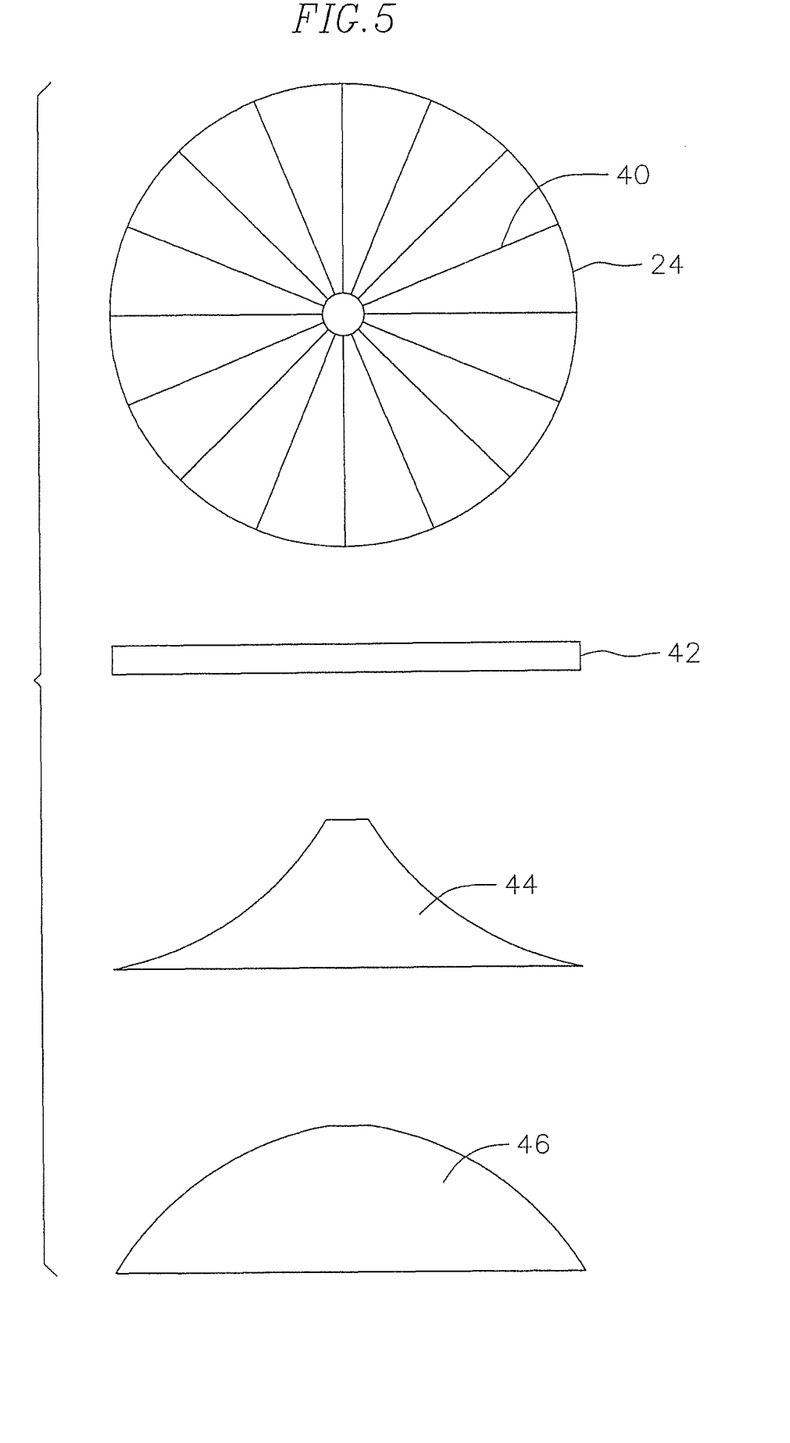
FIG. 5 is a detail view of the circular disk in the dome of FIG. 1 used to divide a growth chamber into two continuous volumes and also illustrates three alternative shapes for the circular disk as flat, concave and convex with respect to an upper volume of the growth chamber.

In order to accommodate a system with illuminated fraction less than one, it becomes necessary to develop a flow pattern that ensures homogeneity of light absorption. This is accomplished by effectively dividing the dome into two continuous domains termed an upper volume 20 and a lower volume 22. The two volumes are separated by a disk 24 suspended by supports 26 from the bottom 28 of the dome that extends out from a central hole 30 toward the edge 32 of the dome. The disk does not extend completely to the dome's edge. This allows for algaculture to flow from the upper volume 20 down into the lower volume 22 outside the disk's circumference. A submerged hydraulic pump 34 located in the central hole 30 of the disk circulates algaculture from the lower volume up along the polar axis. It is this internal pump that will generate the desired flow pattern. Algaculture is forced up along the longest path in the dome, thereby reducing the amount of time spent in the core of the dome's dark zone. When algaculture reaches the top of the dome, the flow can proceed along two paths. Either the flow will exit the dome through the spillover tube 16 or the flow will disperse outward and be forced down along the walls 36 of the dome through the light-rich region of the dome. The flow pattern designated by arrows 37 can be seen in FIG. 4. The disk's shape, position, and curvature relative to the base of the dome can change to better accommodate flow down the walls of the dome. It can also provide the location of a heating and or cooling system. Coils 40 for either task could be imbedded into the disk 24, thereby providing an effect means of controlling temperature given the location of the coils and the nature of the flow inside the dome. FIG. 5 illustrated the coils and possible shapes for the disk 24 including disks that are flat 42, concave 44 and convex 46 to the upper volume 20.

Figure 8:
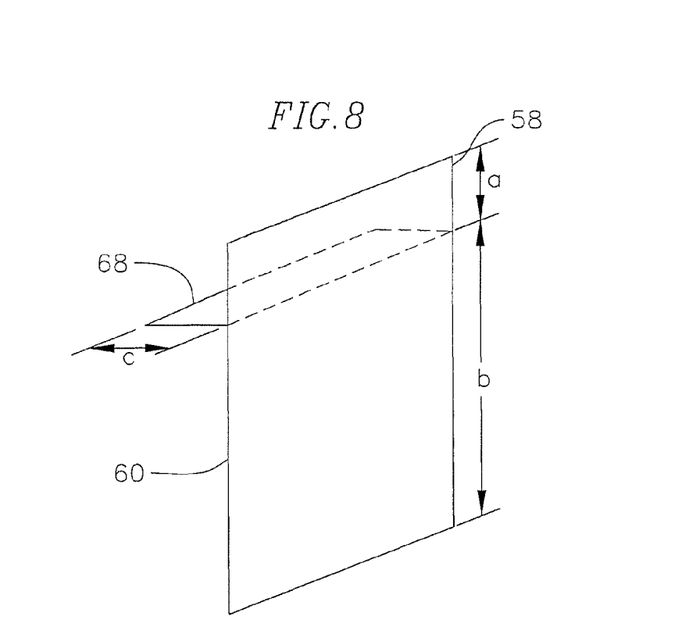
FIG. 8 is a detail view of a typical downcomer of the column of FIG. 6 where a is the weir height, b is the downcomer length, and c is the downcomer arm that allows attachment to a tray.

Continuous flow of algaculture from the column 14 into the dome 12 will cause an equal flow out of the dome's top via the spillover tube 16. Algaculture exiting the dome will flow up through the spillover tube until it reaches the input pipe 48 for the column. At this point, the incline will cease and the algaculture will be dumped into the column. The incline of the spillover and the drop at the column input pipe 48 allow for the removal of any gas present in the dome. This key feature allows the dome to be a completely liquid environment. The algaculture entering the column 14 will pass along the first downcomer 50 before reaching the first stage 52 of the column. The purpose of this first downcomer 50 is to guide algaculture to the first stage 52 and allow for even flow over the stage. FIG. 2 shows two ports representing the algaculture inlet 54 and the air/gas outlet 56 on either side of the dividing first downcomer. A weir 58 at the end of the stage will allow for the retention of a certain volume of liquid-vapor mixture. Continuous flow of algaculture into the stage will force algaculture or froth over the weir down its downcomer 60 to the next stage 62 below. This will continue over each stage and down each downcomer until the algaculture reaches a lower volume 64, or 'reservoir' 65, below the last stage. An example of a typical downcomer 60 can be seen in FIG. 8. The algaculture in this reservoir is then returned to the lower volume 22 of the dome via tube 18 by hydraulic pump 66. Once in the dome's lower volume, light-rich algae from the dome's upper volume and carbon dioxide-rich algaculture from the column will mix before being pump up into the dome's upper volume, thereby restarting the circuit.

Column and Stage Design

Figure 7:
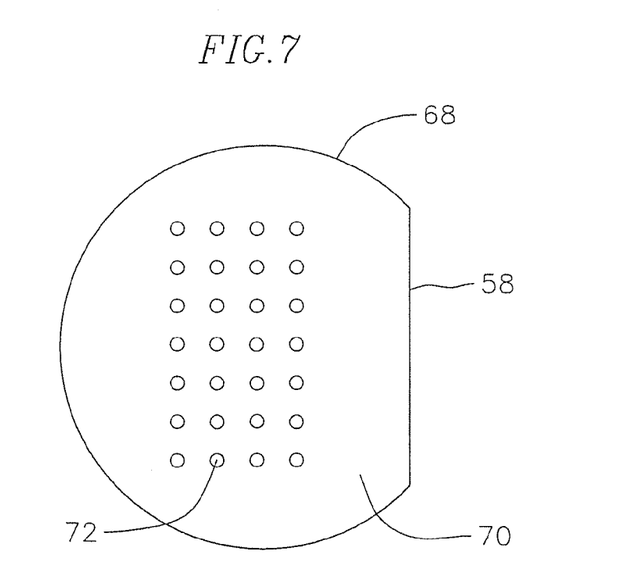
FIG. 7 is a detail view of a tray in one stage of the column of FIG. 6 with perforations to allow gas flow.

Each stage of the column 14 resembles a plate from a trayed column commonly found in chemical distillation columns. An example of this tray 68 can be seen in FIG. 7. The stage comprises a flat surface 70 over which the algaculture will flow and through which gas will bubble via perforations or bubble caps 72. It is this area where the mass transfers of carbon dioxide from air to algaculture and of oxygen from algaculture to air will occur. The weir 58 at the end of the stage allows for the retention of a certain volume of liquid-vapor mixture. The number of stages needed in the column and the number of perforations or bubble caps at each stage are determined by the aeration needs of the total culture as well as the efficiency of each stage. Tray separation height as well as the number of stages may vary according to the environmental and growth conditions.

Figure 9:
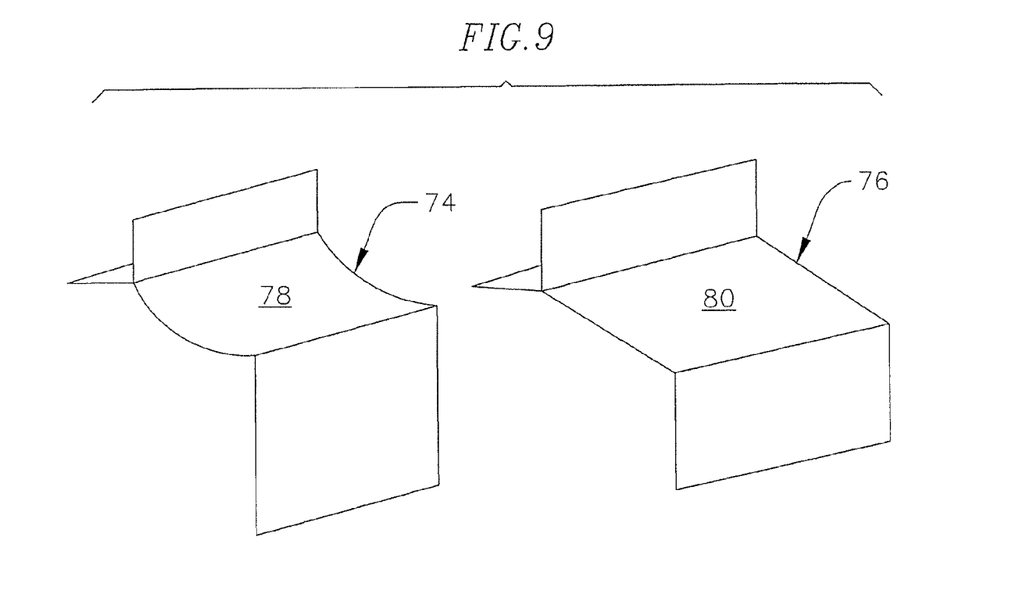
FIG. 9 is a detail view of two alternative designs for the downcomer.

Varying the downcomer surface area can further customize each stage. The volume of the downcomer space dictates the maximum flow rate capable by the entire column. It is possible to design a downcomer 74, 76 with a large top surface area 78, 80 that narrows as it leads to the next stage below. Two such examples can be seen in FIG. 9. In this manner the overall volume does not change much; however, the face of the downcomer can have a greatly increase surface area. This larger downcomer face will aid in separation and harvesting which will be discussed further in the Harvest section below.

Once the algaculture has run its course through the stages of the column, it comes to rest in the lower chamber 64 that represents the remainder of the column volume. A column reservoir ensures adequate algaculture so that the hydraulic pump 66 never run dry, which would cause gas to enter the dome and wear down the hydraulic pump.

The lower volume 64 of the column can also be customized depending on several equipment and design factors. As the designs demonstrate, the reservoir volume 65 of the column holds liquid to some level below the edge of the lowest stage. Filtered air is pumped into a port 82 directly below the lowest stage but above the reservoir volume 65 by a pump 84. The pressure build-up from the introduced air is what supports the liquid culture and prevents weeping through perforations and bubble caps 72. The air pressure is also what drives the flow of gas through these perforations and bubble caps, allowing for mass transfer of carbon dioxide and oxygen. One alternative to the air inlet system is the use of an internal sparger located in the liquid volume of the column reservoir. A sparger 86 would increase the efficiency of mass transfer by converting the column reservoir into an equivalent stage, eliminating the need for one of the stages. This addition may result in increased material and operational costs due to increased pumping. The decision to include this customizable equipment depends on case-based experimentation.

Figure 6:
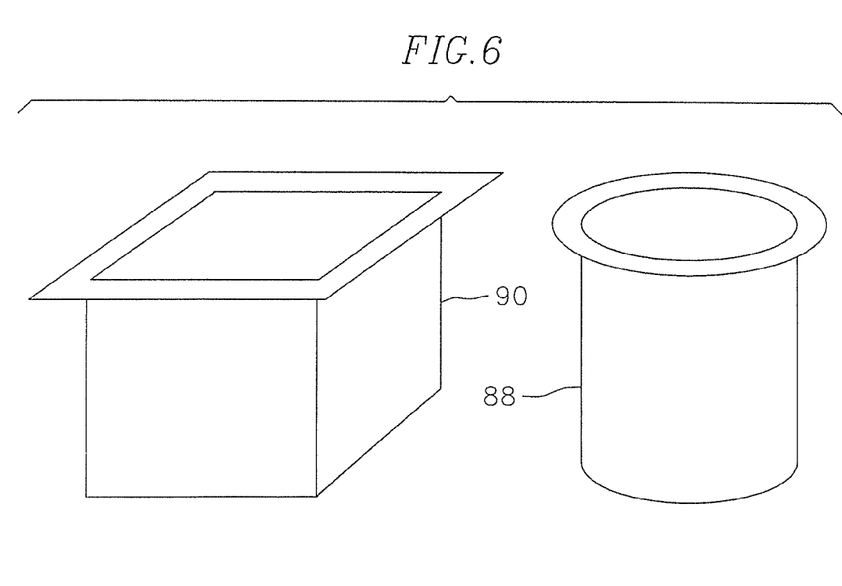
FIG. 6 is a detail view illustrating two examples of the column of FIG. 1.

The column itself may take on a cylindrical shape 88 or rectangular shape 90 as shown in FIG. 6, with internal components adapting correspondingly.

Charging the System

In order to start the growth process, it will be necessary to charge the system with growth media and then to inoculate with a volume of algaculture. One means of accomplishing this task with minimal effect to the equipment described is to place a backflow or check valve 92 upstream from the column-to-dome hydraulic pump. Upstream from this check valve, a tee fitting 94 can be placed to allow fresh media to be pumped into the dome without having backflow into the hydraulic pump. Proper operation of the PBR will require the total volume of the dome to be filled plus additional media corresponding to the total stage and reservoir volume of the column. Once the system is charged with media, it can be inoculated with the starter volume taken from a stock culture. This starter innoculant can be introduced through a rubber membrane port 96 installed on the column. With this system, the PBR can be inoculated using a syringe, providing increased sterility.

Harvest

To provide a semi-continuous production of algae, the separation of algae from culture is designed to occur simultaneous with growth in the column. The harvest of algae from culture is to be carried out using froth flotation, natural buoyancy and other techniques. The addition of a flocculent represents another means of aiding harvest. However, the use of flocculent may cause problems by introducing high levels of metal ions or other growth-inhibiting materials, which will increase the need for regular system turndown. Other methods can be used to induce coagulation in conjunction with froth flotation and flocculation. These techniques include use of a sacrificial electrode and ultrasound irradiation. Any single technique or some combination of those mentioned may result in the most cost effective means of harvest. The utilization of each simply requires the slight modification of the column design.

Froth flotation and algal buoyancy represent the main means of harvest. Increasing the airflow rate can result in the separation of algae from media due to the uptake of dissolved gases. In addition, certain species of algae will accumulate hydrocarbons as they mature, such as fatty acids and oils. These accumulated hydrocarbons will decrease the density of the individual algae, conferring added buoyancy. Following vigorous mixing at each tray, algaculture will slip over to the less turbulent downcomer region. Once in the downcomer region, separation of algae according to buoyancy will occur. 'Mature' algae that are hydrocarbon-rich will remain floating in the top layer of downcomer liquid whereas 'immature' or recently divided algae will flow down to the next stage as part of the algaculture mixture. Some algae species only mature or accumulate hydrocarbons following some perturbation such as silica or nitrogen deprivation. The system will still function as described for these species, it will only require addition operational controlling.

The large downcomer face described earlier will aid in the separation of oil-rich algae. The increased surface area provides the needed plane over which lower-density algae can remain floating while the rest of the algaculture can flow down to the next stage. This large downcomer face also provides the space necessary for an in-column, continuous harvest system. This harvester can be placed in a downcomer region described above or in the column reservoir. The harvester consists of a plastic rectangular funnel 98 that is kept afloat on the surface of the liquid by foam wings 100. This funnel is attached to a vacuum pump 102 located outside the column via flexible tubing 104. During harvest, the vacuum pump will remove the top layer of algaculture as needed. In this manner, the low density, hydrocarbon-rich algae can be removed, thereby lowering the cell density of the system. As previously stated, increasing cell density leads to decreased light penetration while increasing nutrient competition and the stress on the algaculture. By lessening the cell density, the algaculture can maintain or increase its growth rate. Semi-continuous or continuous harvest not only maintains a productive algaculture, it also greatly decreases overhead costs and staves off turndown.

Alga Species

Though this invention remains customizable to fit any species or environment, its design has been engineered with the alga species *Botryococcus braunii* in mind. *B. braunii* is an alga that has gained both praise and criticism as the proposed microalga for biofuel production. *B. braunii* is well known for its production of large amounts of hydrocarbons including long chain isoprenoid triterpenes, such as botryococcenes. When considering fatty acid methyl ester (FAME) based biofuels, such as biodiesel, *B. braunii* is not a promising crop candidate. However, long chain hydrocarbons such as botryoccenes make *B. braunii* an excellent crop candidate for biofuels derived from pyrolytic hydrocracking.

*B. braunii* algae will accumulate the discussed long chain hydrocarbons on the cell surface. Not only does this facilitate extraction, it also aids in harvest. Increasing the oil content of the algae surface makes cell-cell cohesion more favorable as the Zeta potential is greatly reduced. This characteristic makes mature, oil-rich *B. braunii* well suited for separation in the downcomer region of the column. Following separation, hydrocarbons can be extracted from oil-rich *B. braunii* by a number of downstream processes.

Turndown and Sterilization

It is inevitable that the PBR will be shut down for maintenance or scheduled clean-up (turndown). To accommodate this necessity, it is important that the major elements of the invention can be easily disassembled. The dome 12 shown in FIG. 1 consists of two major components: the dome 36 and its base 30. As previously stated, the dome itself will be a transparent material, most likely some sort of plastic, such as acrylic. The material used for the dome base is more variable, but should be sturdy and relatively cheap. The base and dome can be fastened to one another through the use of a flange system 106, 108. This same flange system 110, 112 can also be used to secure the lid 114 of the column to the column structure 116.

Once the PBR 10 has been set up, it will be necessary to sterilize the system before the addition of media. There are several possibilities for accomplishing this task. The most expensive solution is the addition of anti-bacterial and anti-fungal agents to the media regiment. A more creative solution is to pump superheated steam into the system, essentially autoclaving it. Steam will be able to leave the system through installed exhaust ports 118 on the column. Though the steam will be at ambient pressure, the super heated steam should be able to kill any and all microbes.

Although the present invention has been described with respect to several embodiments thereof, it is to be understood that the invention is not to be so limited as changes and modifications can be made therein which are within the scope of the claims herein.

What is claimed is:

1. A dual component closed system photobioreactor for cultivation of photosynthetic organisms in liquid culture comprising:
    a transparent hollow hemi-ellipsoid gasless domed growth chamber having a rigid base for containing the liquid culture for cultivating the photosynthetic organisms;
    the growth chamber includes a rigid internal disk positioned therein defining an upper volume above the disk and a lower volume below the disk and a flow annulus between an outer edge of the disk and an internal surface of the growth chamber, the disk includes a central opening extending therethrough;
    the growth chamber further includes two ports that permit liquid culture flow into and out of the growth chamber;
    a separate trayed column connected to the growth chamber supporting spaced trays attached to and extending from an inside surface of the trayed column for aerating and separating the liquid culture;
    the trayed column is a transparent hollow cylindrical or polyhedron shell having a detachable lid forming an internal volume in which the trays are located and a reservoir is positioned at a bottom of the volume below the trays;
    the trayed column further includes four ports that permit flow of liquid culture and introduced gas into and out of the trayed column;
    means for agitating the liquid culture in the growth chamber between the lower volume and the upper volume through any disk; and
    means for circulation of liquid culture between the growth chamber and the trayed column.

2. The photobioreactor of claim 1, wherein the two ports in the growth chamber comprise a liquid culture exit port located at a top of growth chamber and a liquid culture entrance port positioned on the growth chamber to direct entrance of the liquid culture into the lower volume of the growth chamber.

3. The photobioreactor of claim 1, wherein the hemi-ellipsoid dome permits photosynthetic growth with an, illuminated fraction less than or equal to one.

4. The photobioreactor of claim 1, wherein the means for agitating the liquid culture in the growth chamber includes a submergible pump positioned below the central opening of the disk which drives a flow of liquid culture from the lower volume of the growth chamber through the central opening and into the upper volume of the growth chamber.

5. The photobioreactor of claim 1, wherein the circular disk will permit flow from the upper volume into the lower volume toward the submersible pump through the flow annulus.

6. The photobioreactor of claim 4, wherein the means for circulation further includes the submergible pump that provides circulation within the growth chamber as well as the ports in the growth chamber and the trayed column that permit flow or circulation between the growth chamber and the trayed column.

7. The photobioreactor of claim 6, wherein the means for circulation further includes an external hydraulic pump that drives the liquid culture from the trayed column to the growth chamber.

8. The photobioreactor of claim 1, wherein the four ports of the trayed column include two ports for circulation of liquid culture between the growth chamber and the trayed column, and two ports for the introduction and exhaust of the introduced gas into and out of the trayed column.

9. The photobioreactor of claim 8, wherein the two ports for circulation of liquid culture between the growth chamber and the trayed column include a liquid inlet port positioned above the trays and a liquid outlet port positioned below the trays, and wherein the two ports for introduction and exhaust of introduced gas include a gas inlet port positioned below the trays and a gas outlet port is positioned above the trays.

10. The photobioreactor of claim 1, wherein the trays are, truncated by a perpendicular plate which extends upwardly to form a weir for retention of a certain volume of liquid culture on the trays and also extends downwardly to form a downcomer to direct flow of the liquid culture downwardly within the trayed column.

11. The photobioreactor of claim 1, wherein each tray includes perforations that permit the flow of the introduced gas derived from the gas intake port up and through the tray.

12. The photobioreactor of claim 9, wherein the introduced gas enters the gas intake port by an external air pump.

* * * * *